US006221862B1

(12) United States Patent
Krüger et al.

(10) Patent No.: US 6,221,862 B1
(45) Date of Patent: Apr. 24, 2001

(54) MICROBICIDE 1,4,2-DIOXAZINE DERIVATIVES

(75) Inventors: Bernd-Wieland Krüger, Bergisch Gladbach; Klaus Stenzel, Düsseldorf; Stefan Dutzmann, Langenfeld; Astrid Mauler-Machnik, Leichlingen; Gerd Hänssler, Leverkusen, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/529,070

(22) PCT Filed: Oct. 2, 1998

(86) PCT No.: PCT/EP98/06274

§ 371 Date: Apr. 6, 2000

§ 102(e) Date: Apr. 6, 2000

(87) PCT Pub. No.: WO99/19312

PCT Pub. Date: Apr. 22, 1999

(30) Foreign Application Priority Data

Oct. 14, 1997 (DE) ................................ 197 45 376

(51) Int. Cl.[7] ........................ A61K 31/535; C07D 273/00
(52) U.S. Cl. ............................ 514/229.2; 544/65
(58) Field of Search ..................... 514/229.2; 544/65

(56) References Cited

U.S. PATENT DOCUMENTS

| | | | |
|---|---|---|---|
| 4,808,600 | 2/1989 | Baker et al. | 514/346 |
| 4,895,858 | 1/1990 | Baker et al. | 514/352 |
| 5,679,676 | * 10/1997 | Kruger et al. | 514/229.2 |

FOREIGN PATENT DOCUMENTS

| | | |
|---|---|---|
| 243970 | 11/1987 | (EP) . |
| 617014 | 9/1994 | (EP) . |
| 656351 | 6/1995 | (EP) . |
| 9-12551 | 1/1997 | (JP) . |
| 9-59110 | 3/1997 | (JP) . |
| 9504728 | 2/1995 | (WO) . |
| 96/25406 | 8/1996 | (WO) . |
| 9700862 | 1/1997 | (WO) . |

OTHER PUBLICATIONS

Chem. Abstract CAN 126:27729; Mutat. Res. (month unavailable), 1996, 371(1,2), pp. 87–104, N. Mabon et al, "Monophosphate 32P–Postlabeling Assay Of DNA Adducts From 1,2:3,4–Diepoxybutane, The Most Genotoxic Metabolite Of 1,3–Butadiene: In Vitro Methodological Studies And In Vivo Doslmetry".

Chem. Abstract CAN 126:171587; Jpn. Kokai Tokkyo Koho (month unavailable) 1997, 19 pages, M. Watanabe "Preparation Of Iminothio Ether Compounds As Acaricides And Agrochemical Fungicides".

* cited by examiner

Primary Examiner—Mukund J. Shah
Assistant Examiner—Tamthom N. Truong
(74) Attorney, Agent, or Firm—Joseph C. Gil

(57) ABSTRACT

The invention relates to new thioimides, a process for their preparation and their use as fungicides.

7 Claims, No Drawings

MICROBICIDE 1,4,2-DIOXAZINE DERIVATIVES

It has already been disclosed that certain compounds which are structurally similar to those described below have fungicidal properties (compare, for example, WO 95-04728). However, the fungicidal action of these compounds leaves something to be desired, especially when low amounts are applied.

The new thioimides of the general formula (I),

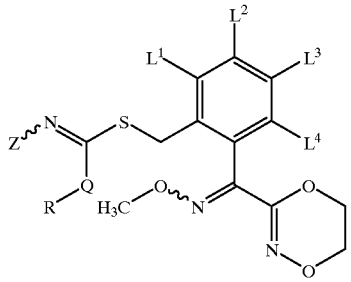

(I)

in which
Q represents a single bond, oxygen or sulphur,
R represents alkyl or optionally substituted cycloalkyl having 3 to 5 carbon atoms,
Z represents in each case optionally substituted cycloalkyl, aryl, arylalkyl, heterocyclyl or heterocyclylalkyl and
$L^1, L^2, L^3$ and $L^4$ are identical or different and independently of one another in each case represent hydrogen, halogen, cyano, nitro or in each case optionally halogen-substituted alkyl, alkoxy, alkylthio, alkylsulphinyl or alkylsulphonyl have now been found.

In the definitions, the saturated or unsaturated hydrocarbon chains, such as alkyl, also when linked with heteroatoms, such as in alkoxy or alkylthio, are in each case straight-chain or branched.

Halogen in general represents fluorine, chlorine, bromine or iodine, preferably fluorine, chlorine or bromine, in particular fluorine or chlorine.

Heterocyclyl represents saturated or unsaturated and aromatic, cyclic compounds, in which at least one ring member is a heteroatom, that is to say an atom other than carbon. If the ring contains several heteroatoms, these can be identical or different. Heteroatoms are preferably oxygen, nitrogen or sulphur. If the ring contains several oxygen atoms, these are not adjacent. If appropriate, the cyclic compounds form a polycyclic ring system together with other carbocyclic or heterocyclic, fused-on or bridged rings. Mono- or bicyclic ring systems are preferred, in particular mono- or bicyclic, aromatic ring systems.

It has furthermore been found that the new thioimides of the general formula (I) are obtained by a process in which thioamides of the general formula (II)

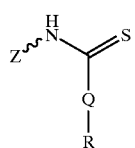

(II)

in which
Q, R and Z have the abovementioned meanings, are reacted with a halogenomethyl compound of the general formula (III)

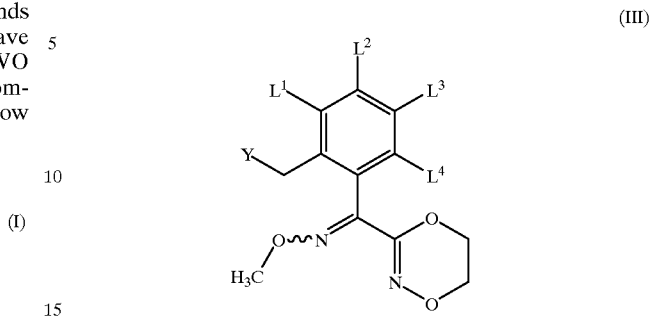

(III)

in which
$L^1$, $L^2$, $L^3$ and $L^4$ have the abovementioned meanings and
Y represents halogen,
optionally in the presence of a diluent and optionally in the presence of an acid acceptor.

Finally, it has been found that the new thioimides of the general formula (I) show a very potent fungicidal action.

Where appropriate, the compounds according to the invention can be in the form of mixtures of various possible isomeric forms, in particular of stereoisomers, such as, for example, E and Z isomers, or optical isomers. Both the E and the Z isomers, the individual enantiomers, the racemates and also any desired mixtures of these isomers are claimed.

Preferred thioimides of the formula (I) are those in which
Q represents a single bond, oxygen or sulphur,
R represents alkyl having 1 to 4 carbon atoms or cycloalkyl having 3 to 6 carbon atoms which is optionally mono-substituted to tetrasubstituted by halogen or alkyl,
Z represents cycloalkyl or cycloalkylalkyl which has in each case 3 to 7 carbon atoms in the cycloalkyl part and 1 to 4 carbon atoms in the alkyl part and is in each case optionally monosubstituted to tetrasubstituted by halogen or alkyl;
or represents heterocyclyl or heterocyclylalkyl which has in each case 3 to 7 ring members and 1 to 4 carbon atoms in the alkyl part and is optionally substituted by halogen or alkyl having 1 to 4 carbon atoms;
or represents aryl or arylalkyl which has in each case 6 to 10 carbon atoms in the aryl part and 1 to 4 carbon atoms in the alkyl part and is in each case optionally monosubstituted to tetrasubstituted in an identical or different manner in the aryl part, the possible substituents preferably being chosen from the following list:
halogen, cyano, nitro, amino, formyl, carbamoyl, thiocarbamoyl;
in each case straight-chain or branched alkyl, alkoxy, alkoxyalkyl, alkylthioalkyl, alkylaminoalkyl, dialkylaminoalkyl, alkylthio, alkylsulphinyl or alkylsulphonyl having in each case 1 to 8 carbon atoms;
in each case straight-chain or branched alkenyl or alkenyloxy having in each case 2 to 6 carbon atoms;
in each case straight-chain or branched halogenoalkyl, halogenoalkoxy, halogenoalkylthio, halogenoalkylsulphinyl or halogenoalkylsulfonyl having in each case 1 to 6 carbon atoms and 1 to 13 identical or different halogen atoms;
in each case straight-chain or branched halogenoalkenyl or halogenoalkenyl-oxy having in each case 2 to 6 carbon atoms and 1 to 11 identical or different halogen atoms;
in each case straight-chain or branched alkylamino or dialkylamino;

alkylcarbonyl, alkoxycarbonyl, alkylaminocarbonyl, dialkylaniinocarbonyl, arylalkylaminocarbonyl, alkenylcarbonyl or alkinylcarbonyl, having 1 to 6 carbon atoms in the particular hydrocarbon chains;

cycloalkyl or cycloalkyloxy having in each case 3 to 6 carbon atoms;

in each case divalent alkylene having 3 or 4 carbon atoms, oxyalkylene having 2 or 3 carbon atoms or dioxyalkylene having 1 or 2 carbon atoms, in each case optionally monosubstituted to tetrasubstituted in an identical or different manner by fluorine, chlorine, oxo, methyl, trifluoromethyl or ethyl;

or a grouping

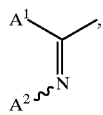

wherein $A^1$ represents hydrogen or alkyl having 1 to 4 carbon atoms or cycloalkyl having 3 to 6 carbon atoms and $A^2$ represents hydroxyl, amino, methylamino, methyl, phenyl, benzyl, alkoxy, alkylamino or dialkylamino having 1 to 4 carbon atoms in the particular alkyl chains and $L^1, L^2, L^3$ and $L^4$ are identical or different and independently of one another in each case represent hydrogen, halogen, cyano, nitro or alkyl, alkoxy, alkylthio, alkylsulphinyl or alkylsulphonyl which has in each case 1 to 6 carbon atoms and is in each case optionally substituted by 1 to 5 halogen atoms, preferably hydrogen or methyl, and in particular hydrogen.

Particularly preferred thioimides of the formula (I) are those in which

Q represents a single bond, oxygen or sulphur and

R represents methyl, ethyl, n- or i-propyl or, in particular, cyclopentyl, cyclobutyl or, in particular, cyclopropyl, in each case optionally monosubstituted to tetrasubstituted by fluorine, chlorine, methyl and/or ethyl.

Thioimides of the formula (I) which are also particularly preferred are those in which Z represents cyclopentyl or cyclohexyl, in each case optionally monosubstituted to tetrasubstituted by fluorine, chlorine, methyl or ethyl;

or represents thienyl, pyridyl, furyl, thienylmethyl, pyridylmethyl or furylmethyl, optionally substituted by methoxy, methyl, ethyl, fluorine, chlorine or bromine;

or represents benzyl, 1-phenylethyl or 2-phenylethyl, in each case optionally monosubstituted to tetrasubstituted in an identical or different manner, and in particular represents optionally substituted phenyl, the possible substituents preferably being chosen from the following list:

fluorine, chlorine, bromo, cyano, nitro, amino, formyl, carbamoyl, thiocarbamoyl, methyl, ethyl, n- or i-propyl, n-, i-, s- or t-butyl, methoxymethyl, methoxy, ethoxy, n- or i-propoxy, methylthio, ethylthio, n- or i-propylthio, methylsulphinyl, ethylsulphinyl, methylsulphonyl or ethylsulphonyl, methylaminomethyl, dimethylaminomethyl, vinyl, allyl, 2-methylallyl, propen-1-yl, crotonyl, propargyl, vinyloxy, allyloxy, 2-methylallyloxy, propen-1-yloxy, crotonyloxy, propargyloxy;

trifluoromethyl, trifluoroethyl, difluoromethoxy, trifluoromethoxy, difluorochloromethoxy, trifluoroethoxy, pentafluoroethoxy, 2-chloro-1,1,2-trifluoroethoxy, difluoromethylthio, trifluoromethylthio, difluorochloromethylthio, trifluoromethylsulphinyl or trifluoromethylsulphonyl, methylamino, ethylamino, n- or i-propylamino, dimethylamino, diethylamino, acetyl, propionyl, methoxycarbonyl, ethoxycarbonyl, methylaminocarbonyl, ethylaminocarbonyl, dimethylaminocarbonyl, diethylaminocarbonyl, acryloyl, propioloyl, cyclopentyl, cyclohexyl, in each case divalent propanediyl, ethyleneoxy, methylenedioxy or ethylenedioxy, in each case optionally monosubstituted to tetrasubstituted in an identical or different manner by fluorine, chlorine, oxo, methyl or trifluoromethyl, or a grouping

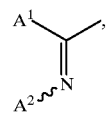

wherein $A^1$ represents hydrogen or methyl and $A^2$ represents hydroxyl, methoxy, ethoxy, amino, methylamino, methyl, phenyl or benzyl.

Compounds of the formula (I) which are also particularly preferred are those in which $L^1, L^2, L^3$ and $L^4$ are identical or different and independently of one another in each case represent hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, preferably hydrogen or methyl, and in particular hydrogen.

Particularly preferred compounds of the formula (I) are those in which

Q represents sulphur, and in particular represents a single bond.

The definitions of radicals given above generally or stated in the preferred ranges apply both to the end products of the formula (I) and correspondingly to the particular starting substances or intermediate products required for the preparation.

These definitions of radicals can be combined with one another as desired, that is to say also between the stated ranges of preferred compounds.

Formula (II) provides a general definition of the thioamides required as starting substances for carrying out the process according to the invention. In this formula (II), Q, R and Z preferably or in particular have those meanings which have already been mentioned as preferred or as particularly preferred for R and Z in connection with the description of the compounds of the formula (I) according to the invention.

The thioamides of the formula (II) are known and can be prepared by known processes (compare, for example, JP 09012551, CA: 126:171587; EP-A 243971; EP-A243970; JP 09059110; CA: 126:277279).

Formula (III) provides a general definition of the halogenomethyl compounds furthermore required as starting substances for carrying out the process according to the invention. In this formula (III), $L^1$, $L^2$, $L^3$ and $L^4$ preferably or in particular have those meanings which have already been mentioned as preferred or as particularly preferred for $L^1$, $L^2$, $L^3$ and $L^4$ in connection with the description of the compounds of the formula (I) according to the invention. Y represents halogen, preferably chlorine or bromine.

The halogenomethyl compounds of the formula (III) are obtained by a process in which, for example, phenoxy compounds of the general formula (IV)

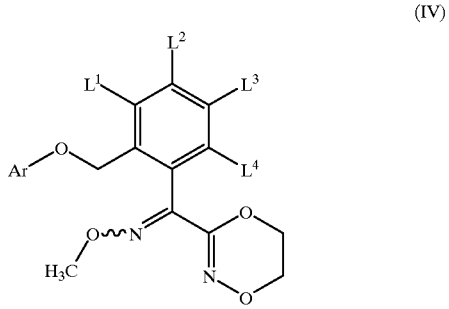

(IV)

in which
$L^1$, $L^2$, $L^3$ and $L^4$ have the abovementioned meanings and Ar represents optionally substituted phenyl,
are reacted with a carboxylic acid halide, such as, for example, acetylchloride, optionally in the presence of a diluent, such as, for example, methylene chloride, and optionally in the presence of a Lewis acid, such as, for example, aluminium chloride.

The phenoxy compounds of the formula (IV) are known and/or can be prepared by known methods (compare, for example, WO-A 9504728 and DE-A 19504625).

Possible diluents for carrying out the process according to the invention are all the inert organic solvents. These include, preferably, aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methyl-pyrrolidone or hexamethylphosphoric acid triamide; esters, such as methyl acetate or ethyl acetate; sulphoxides, such as dimethylsulphoxide, or sulphones, such as sulpholane.

The reaction temperatures can be varied within a substantial range in the carrying out of the process according to the invention. In general, the reaction is carried out at temperatures from −50° C. to 100° C., preferably at temperatures from −20° C. to 50° C. For carrying out the process according to the invention for the preparation of the compounds of the formula (I), in general 0.5 to 5 mol, preferably 0.8 to 2 mol, of halogenomethyl compound of the formula (III) are employed per mol of thioamide of the formula (II).

The process according to the invention is in general carried out under normal pressure. However, it is also possible to carry out the process under increased or reduced pressure—in general between 0.1 bar and 10 bar.

The reaction is carried out and the reaction products are worked up and isolated by generally customary processes (compare also the preparation examples).

The substances according to the invention have a potent microbicidal action and can be employed for combating undesirable microorganisms, such as fungi and bacteria, in plant protection and in the preservation of material.

Fungicides can be employed in plant protection for combating Plasmodiophoromycetes, Oomycetes, Chytridiomycetes, Zygomycetes, Ascomycetes, Basidiomycetes and Deuteromycetes.

Bactericides can be employed in plant protection for combating Pseudomonadaceae, Rhizobiaceae, Enterobacteriaceae, Corynebacteriaceae and Streptomycetaceae.

Some causative organisms of fungal and bacterial diseases which fall under the generic names listed above may be mentioned as examples but not by way of limitation:
Xanthomonas species: such as, for example, *Xanthomonas campestris* pv. oryzae;
Pseudomonas species, such as, for example *Pseudomonas syringae* pv. lachrymans;
Erwinia species, such as, for example, *Erwinia amylovora;*
Pythium species, such as, for example, *Pytium ultimum;*
Phytophthora species, such as, for example, *Phytophthora infestans;*
Pseudoperonospora species, such as, for example, *Pseudoperonospora humuli* or *Pseudoperonospora cubensis;*
Plasmopara species, such as, for example, *Plasmopara viticola;*
Bremia species, such as, for example, *Bremia lactucae;*
Peronospora species, such as, for example, *Peronospora pisi* or *P. brassicae;*
Erysiphe species, such as, for example, *Erysiphe graminis;*
Sphaerotheca species, such as, for example, *Sphaerotheca fuliginea;*
Podosphaera species, such as, for example, *Podosphaera leucotricha;*
Venturia species, such as, for example, *Venturia inaequalis;*
Pyrenophora species, such as, for example, *Pyrenophora teres* or *P. graminea* (conidia form: Drechslera, syn: Helminthosporium);
Cochliobolus species, such as, for example, *Cochliobolus sativus* (conidia form: Drechslera, syn: Helminthosporium);
Uromyces species, such as, for example, *Uromyces appendiculatus;*
Puccinia species, such as, for example, *Puccinia recondita;*
Sclerotinia species, such as, for example, *Sclerotinia sclerotiorum;*
Tilletia species, such as, for example, *Tilletia caries;*
Ustilago species, such as, for example, *Ustilago nuda* or *Ustilago avenae;*
Pellicularia species, such as, for example, *Pellicularia sasakii;*
Pyricularia species, such as, for example, *Pyricularia oryzae;*
Fusarium species, such as, for example, *Fusarium culmorum;*
Botrytis species, such as, for example, *Botrytis cinerea;*
Septoria species, such as, for example, *Septoria nodorum;*
Leptosphaeria species, such as, for example, *Leptosphaeria nodorum;*
Cercospora species, such as, for example, *Cercospora canescens;*
Altemaria species, such as, for example, *Altemaria brassicae;*

Pseudocercosporella species, such as, for example, *Pseudocercosporella herpotrichoides.*

The good plant tolerance of the active compounds in the concentrations necessary for combating plant diseases allows a treatment of above-ground parts of plants, of vegetative propagation stock and seeds, and of the soil.

The active compounds according to the invention can be employed with particularly good success here for combating cereal diseases, such as, for example, against Leptosphaeria or Puccinia species, diseases in vine-, fruit- and vegetable-growing, such as, for example, against Phytophtora or Plasmopara species, or rice diseases, such as, for example, against Pyricularia species. The active compounds according to the invention furthermore have a very potent and broad in vitro action.

The active compounds according to the invention are also suitable for increasing the harvest yield. Moreover, they are of low toxicity and have a good plant tolerance.

The active compounds can be converted into the customary formulations, depending on their particular physical and/or chemical properties, such as solutions, emulsions, suspensions, powders, foams, pastes, granules, aerosols, microencapsulations in polymeric substances and in coating compositions for seed, and ULV cold and warm mist formulations.

These formulations are prepared in a known manner, for example by mixing the active compounds with extenders, that is to say liquid solvents, liquefied gases under pressure and/or solid carriers, optionally using surface-active agents, that is to say emulsifying agents and/or dispersing agents and/or foam-forming agents. In the case where water is used as an extender, organic solvents, for example, can also be used as auxiliary solvents. Possible liquid solvents are essentially: aromatics, such as xylene, toluene or alkylnaphthalenes, chlorinated aromatics or chlorinated aliphatic hydrocarbons, such as chlorobenzenes, chloroethylenes or methylenechloride, aliphatic hydrocarbons, such as cyclohexane or paraffins, for example mineral oil fractions, alcohols, such as butanol, or glycol and ethers and esters thereof, ketones, such as acetone, methyl ethyl ketone, methyl isobutyl ketone or cyclohexanone, strongly polar solvents, such as dimethylformamide and dimethylsulphoxide, and water. Liquefied gaseous extenders or carriers are understood as meaning those liquids which are gaseous at normal temperature and under normal pressure, for example aerosol propellant gases, such as halogenohydrocarbons and butane, propane, nitrogen and carbon dioxide. Possible solid carriers are: for example, naturally occurring rock powders, such as kaolins, aluminas, talc, chalk, quartz, attapulgite, montmorillonite or diatomaceous earth, and synthetic rock powders, such as highly disperse silicic acid, aluminium oxide and silicates. Possible solid carriers for granules are: for example, crushed and fractionated naturally occurring rocks, such as calcite, marble, pumice, sepiolite and dolomite, and synthetic granules of inorganic and organic flours, as well as granules of organic material, such as sawdust, coconut shells, maize cobs and tobacco stalks. Possible emulsifying and/or foam-forming agents are: for example, nonionic and anionic emulsifiers, such as polyoxyethylene fatty acid esters, polyoxyethylene fatty alcohol ethers, for example alkylarylpolyglycol ethers, alkylsulphonates, alkyl sulphates, aryl sulphonates and protein hydrolysates. Possible dispersing agents are: for example, lignin-sulphite waste liquors and methylcellulose.

Adhesives, such as carboxymethylcellulose, naturally occurring and synthetic pulverulent, granular or latex-like polymers, such as gum arabic, polyvinyl alcohol and polyvinyl acetate, and naturally occurring phospholipids, such as cephalins and lecithins, and synthetic phospholipids can be used in the formulations. Other additives can be mineral and vegetable oils.

It is possible to use dyestuffs, such as inorganic pigments, for example iron oxide, titanium oxide and Prussian blue, and organic dyestuffs, such as alizarin, azo and metal phthalocyanine dyestuffs, and trace nutrients, such as salts of iron, manganese, boron, copper, cobalt, molybdenum and zinc.

The formulations in general comprise between 0.1 and 95 percent by weight of active compound, preferably between 0.5 and 90%.

The active compounds can be converted into the customary formulations, depending on their particular physical and/or chemical properties, such as solutions, emulsions, suspensions, powders, foams, pastes, granules, aerosols, microencapsulations in polymeric substances and in coating compositions for seed, and ULV cold and warm mist formulations.

The active compounds according to the invention can also be used, as such or in their formulations, as a mixture with known fungicides, bactericides, acaricides, nematicides or insecticides, in order thus, for example, to broaden the activity spectrum or to prevent development of resistance. In many cases, synergistic effects are obtained here, that is to say the activity of the mixture is greater than the activity of the individual components.

Possible mixing partners are, for example, the following compounds:

Fungicides aldimorph, ampropylfos, ampropylfos-potassium, andoprim, anilazin, azaconazole, azoxystrobin, benalaxyl, benodanil, benomyl, benzamacril, benzamacrylisobutyl, bialaphos, binapacryl, biphenyl, bitertanol, blasticidin-S, bromuconazole, bupirimat, buthiobat, calcium polysulphide, capsimycin, captafol, captan, carbendazim, carboxin, carvon, chinomethionat (quinomethionate), chlobenthiazon, chlorfenazole, chloroneb, chloropicrin, chlorothalonil, chlozolin at, clozylacon, cufraneb, cymoxanil, cyproconazole, cyprodinil, cyprofuram, debacarb, dichlorophen, diclobutrazole, diclofluanid, diclomezin, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, ediphenphos, epoxiconazole, etaconazole, ethirimol, etridiazole, famoxadon, fenapanil, fenarimol, fenbuconazol, fenfraim, fenitropan, fenpiclonil, fenpropidin, fenpropimorph, fentinacetate, fentin hydroxide, ferbam, ferimzon, fluazinam, flumetover, fluoromid, fluquinconazole, flurprimidol, flusilazole, flusulfamide, flutolanil, flutriafol, folpet, fosetyl-aluminium, fosetyl-sodium, fthalid, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilat, iminoctadine triacetate, iodocarb, ipconazole, iprobenfos (IBP), iprodione, irumamycin, isoprothiolan, isovaledione, kasugamycin, kresoxime-methyl, copper formulations, such as copper hydroxide, copper naphthenate, copper oxychloride, copper sulphate, copper oxide, oxine-copper and Bordeaux mixture,
mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin,
nickel-dimethyldithiocarbamate, nitrothal-isopropyl, nuarimol,
ofurace, oxadixyl, oxamocarb, oxolinic acid, oxycarboxim, oxyfenthiin,
paclobutrazole, pefurazoate, penconazole, pencycuron, phosdiphen, pimaricin, piperalin, polyoxin, polyoxorim, probenazole, prochloraz, procymidon, propamocarb, propanosine-sodium, propiconazole, propineb, pyrazophos, pyrifenox, pyrimethanil, pyroquilon, pyroxyfur,
quinconazole, quintozen (PCNB),
sulphur and sulphur formulations,
tebuconazole, tecloftalam, tecnazene, tetcyclacis, tetraconazole, thiabendazole, thicyofen, thifluzamide, thiophanate-methyl, thiram, tioxymid, tolclofo-methyl, tolylfluanid, triadimefon, triadimenol, triazbutil, triazoxide, trichlamide, tricyclazole, tridemorph, triflumizol, triforin, triticonazole,
uniconazole,
validamycin A, vinclozolin, viniconazole,
zarilamid, zineb, Ziram and
Dagger G,
OK-8705,
OK-8801,
α-(1,1-dimethylethyl)-β-(2-phenoxyethyl)-1H-1,2,4-triazole-1-ethanol,
α-(2,4-dichlorophenyl)-β-fluoro-β-propyl-1H-1,2,4-triazole-1-ethanol,
α-(2,4-dichlorophenyl)-β-methoxy-α-methyl-1H-1,2,4-triazole-1-ethanol,
α-(5-methyl-1,3-dioxan-5-yl)-β-[[4-(trifluoromethyl)-phenyl]-methylene]-1H-1,2,4-triazole-1-ethanol,
(5RS,6RS)-6-hydroxy-2,2,7,7-tetramethyl-5-(1H-1,2,4-triazol-1-yl)-3-octanone,
(E)- α-(methoxyimino)-N-methyl-2-phenoxy-phenylacetamide,
{2-methyl-1-[[[1-(4-methylphenyl)-ethyl]-amino]-carbonyl]-propyl}-carbamic acid-1-isopropylester
1-(2,4-dichlorophenyl)-2-(1H-1,2,4-triazol-1-yl)-ethanone-O-(phenylnethyl) oxime,
1-(2-methyl-1-naphthalenyl)-1H-pyrrole-2,5-dione,
1-(3,5-dichlorophenyl)-3-(2-propenyl)-2,5-pyrrolidinedione,
1-[(diiodomethyl)-sulphonyl]-4-methyl-benzene,
1-[[2-(2,4-dichlorophenyl)-1,3-dioxolan-2-yl]-methyl]-1H-imidazole,
1-[[2-(4-chlorophenyl)-3-phenyloxiranyl]-methyl]-1H-1,2,4-triazole,
1-[1-[2-[(2,4dichlorophenyl)-methoxy]-phenyl]-ethenyl]-1H-imidazole,
1-methyl-5-nonyl-2-(phenylmethyl)-3-pyrrolidinole,
2',6'-dibromo-2-methyl-4'-trifluoromethoxy-4'-trifluoro-methyl-1,3-thiazole-5-carboxanilide,
2,2-dichloro-N-[1-(4-chlorophenyl)ethyl]-1-ethyl-3-methyl-cyclopropanecarboxamide,
2,6-dichloro-5-(methylthio)4-pyrimidinyl thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)-sulphonyl]-5-(trichloromethyl)-1,3,4-thiadiazole,
2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile,
2-aminobutane,
2-bromo-2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol(OPP),
3,4-dichloro-1-[4-(difluoromethoxy)-phenyl]-1H-pyrrole-2,5-dione,
3,5-dichloro-N-[cyano[(1-methyl-2-propynyl)-oxy]-methyl]-benzamide,
3-(1,1-dimethylpropyl-1-oxo-1H-indene-2-carbonitrile,
3-[2-(4-chlorophenyl)-5-ethoxy-3-isoxazolidinyl]-pyridine,
4-chloro -2-cyano-N,N-dimethyl-5-(4-methylphenyl)-1H-imidazole-1-sulphonamide,
4-methyl-tetrazolo[1,5-a]quinazolin-5(4H)-one,
8-(1,1-dimethylethyl)-N-ethyl-N-propyl-1,4-dioxaspiro[4.5]decan-2-methanamine,
8-hydroxyquinoline sulphate,
9H-xanthene-9-carboxylic acid 2-[(phenylamino)-carbonyl]-hydrazide,
bis-(1-methylethyl)-3-methyl-4-[(3-methylbenzoyl)-oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholine hydrochloride,
ethyl [(4-chlorophenyl)azo]-cyanoacetate,
potassium bicarbonate,
methanetetrathiol sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide.
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidinamine,
N-(4-hexylphenyl)-1,4,5,6-tetrahydro-2-pyrimidinamine,
N-(5-chloro-2-methylphenyl)-2-methoxy-N-(2-oxo-3-oxazolidinyl)-acetamide,
N-(6-methoxy)-3-pyridinyl)-cyclopropanecarboxamide,
N-[2,2,2-trichloro-1-[(chloroacetyl)-amino]-ethyl]-benzamide,
N-[3-chloro-4,5-bis-(2-propinyloxy)-phenyl]-N'-methoxy-methanimide-amide,
N-formyl-N-hydroxy-DL-alanine sodium salt,
O,O-diethyl [2-(dipropylamino)-2-oxoethyl]-ethylphosphoramidothioate,
O-methyl S-phenyl-phenylpropylphosphoramidothioate,
S-methyl 1,2,3-benzothiadiazole-7-carbothioate,
spiro[2H]-1-benzopyran-2,1'(3'H)-isobenzofuran]-3'-one, Bactericides bronopol, dichlorophen, nitrapyrin, nickel-dimethyldithiocarbamate, kasugamycin, octhilinon, furan-carboxylic acid, oxytetracycline, probenazole, streptomycin, tecloftalam, copper sulphate and other copper formulations.

Insecticides/acaricides/nematicides abamectin, acephate, acrinathrin, alanycarb, aldicarb, alphamethrin, amitraz, avemectin, AZ 60541, azadirachtin, azinphos A, azinphos M, azocyclotin, Bacillus thuringiensis, 4-bromo-2-(4-chlorophenyl)-1-(ethoxymethyl)-5-(trifluoro-methyl)-1H-pyrrole-3-carbonitrile, bendiocarb, benfuracarb, bensultap, betacyfluthrin, bifenthrin, BPMC, brofenprox, bromophos A, bufencarb, buprofezin, butocarboxim, butylpyridaben, cadusafos, carbaryl, carbofuran, carbophenothion, carbosulfan, cartap, chloethocarb, chloroethoxyfos, chlorofenapyr, chlorofenvinphos, chlorofluazuron, chloromephos, N-[(6-chloro-3-pyridinyl)-methyl]-N'-cyano-N-methyl-ethanimide-amide, chloropyrifos, chloropyrifos M, cis-resmethrin, clocytlrin, clofentezin, cyanophos, cycloprothrin, cyfluthrin, cyhalothrin, cyhexatin, cypermethrin, cyromazine, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lamda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, nitenpyram omethoate, oxamyl, oxydemethon M, oxydeprofos, parathion A, parathion M, permethrin, phenthoate, phorate, phosalon, phosmet, phosphamidon, phoxim, pirimicarb, pirimiphos M, pirimiphos A, profenophos, promecarb, propaphos, propoxur, prothiophos, prothoate, pymetrozine, pyrachlophos, pyridaphenthion, pyresmethrin, pyrethirum, pyridaben, pyrimidifen, pyriproxifen, quinalphos, salithion, sebufos, silafluofen, sulfotep, sulprofos, tebufenozide, tebufenpyrad, tebupirimiphos, teflubenzuron, tefluthrin, temephos, terbam, terbufos, tetrachlorovinphos, thiafenox, thiodicarb, thiofanox, thiomethon, thionazin, thuringiensin, tralomethrin, triarathen, triazophos, triazuron, trichlorofon, triflumuron, trimethacarb, vamidothion, XMC, xylylcarb, zetamethrin.

A mixture with other known active compounds, such as herbicides, or with fertilizers and growth regulators is also possible.

The active compounds can be used as such, in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. Seeds of plants can also be treated.

When the active compounds according to the invention are employed as fungicides, the amounts applied can be varied within a substantial range, depending on the method of application. In the case of treatment of parts of plants, the amounts of active compound applied are in general between 0.1 and 10,000 g/ha, preferably between 10 and 1,000 g/ha. In the treatment of seed, the amounts of active compound applied are in general between 0.001 and 50 g per kilogram of seed, preferably between 0.01 and 10 g per kilogram of seed. In the treatment of soil, the amounts of active compound applied are in general between 0.1 and 10,000 g/ha, preferably between 1 and 5,000 g/ha.

Preparation Examples

EXAMPLE (1)

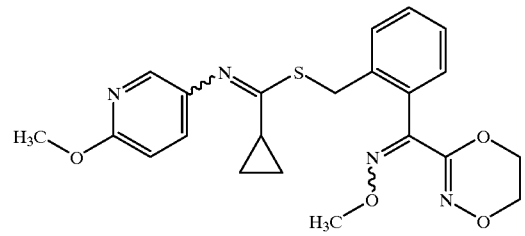

0.0865 g (0.0024 mol) of an 80% strength sodium hydride suspension is added to a solution of 0.5 g (0.0024 mol) of cyclopropanethiocarboxylic acid (6-methoxypyridin-3-yl)-amide in 20 ml of dimethylformamide at 0° C. and the mixture is stirred for 5 minutes. A solution of 0.65 g (0.0024 mol) of (2-chloromethylphenyl)-(5,6-dihydro-[1,4,2] dioxazin-3-yl)-methanone 0-methyl oxime in 10 ml of dimethylformamide is added and the mixture is stirred for a further 18 hours without further cooling. The mixture is poured into 200 ml of water and extracted three times with 150 ml of ethyl acetate each time. The combined organic phases are washed twice with 100 ml of water each time, dried over magnesium sulphate and concentrated under reduced pressure. The residue is chromatographed over silica gel with cyclohexane/ethyl acetate (4:1). 1.0 g (95% of theory) of N-(6-methoxy-pyridin-3-yl)-cyclopropanecarboximic acid 2-[(5,6-dihydro-[1,4,2] dioxazin-3-yl)-methoxyimino-methyl]-benzyl ester is obtained.

HPLC: logP=3.04

The logP values were determined in accordance with EEC Directive 79/831 Annex V. A8 by HPLC (gradient method, acetonitrile/0.1% strength aqueous phosphoric acid)

The compounds of the formula (I-a) according to the invention listed in the following table 1 are also obtained analogously to Example (I) and in accordance with the general description of the preparation process according to the invention:

(I-a)

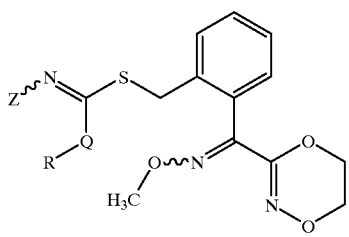

TABLE 1

| Example | Q | R | Z | logP |
|---|---|---|---|---|
| 2 | — | Cyclopropyl | 4-Methoxyphenyl | 3.16 |
| 3 | — | Cyclopropyl | 2-Trifluoromethylphenyl | 4.16 |
| 4 | — | (cyclopropyl with CH3, H5C2, Cl, Cl) | (H3C-CH-phenyl-Cl) | 5.7 |
| 5 | S | Methyl | (pyridyl-OCH3) | 3.15 |

Preparation of precursors of the formula (IV)

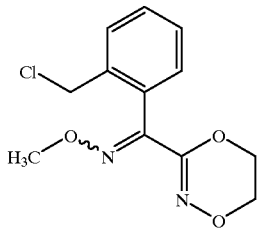

61.1 g (0.775 mol) of acetyl chloride are added to a suspension of 103.4 g (0.775 mol) of anhydrous aluminum chloride in 1 l of methylene chloride in the course of 15 minutes. A solution of 105 g (0.31 mol) of (5,6-dihydro-[1,4,2]dioxazin-3-yl)-(2-o-tolyloxymethyl-phenyl)-methanone O-methyl oxime in 500 ml of methylene chloride is added dropwise to this mixture at 20° C. under argon, the reaction mixture heating up to 30° C., and the mixture is stirred for a further 3 hours. The reaction mixture is poured onto 2 l of ice-water and extracted 3 times with 300 ml of methylene chloride each time. The combined organic phases are dried over magnesium sulphate and concentrated under reduced pressure. The residue is stirred with diisopropylether and the solid formed is filtered off with suction (59.1 g). The filtrate is concentrated under reduced pressure and the residue is chromatographed over silica gel with cyclohexane/ethyl acetate (3:1). A further 4 g of product are obtained. 63.1 g (76% of theory) of (2-chloromethyl-phenyl)-(5,6-dihydro-[1,4,2]dioxazin-3-yl)-methanone O-methyl oxime are obtained in total.

$^1$H-NMR (CDCl$_3$, TMS): δ=3.99; 4.17–4.20; 4.49–4.53; 7.15–7.53 ppm.

Use Examples

EXAMPLE A

Phytophthora test (tomato)/protective
Solvent: 47 parts by weight of acetone
Emulsifier: 3 parts by weight of alkylaryl polyglycol ether To prepare an appropriate formulation of the active compound, 1 part by weight of active compound is mixed with the stated amounts of solvent and emulsifier, and the concentrate is diluted with water to the desired concentration.

To test for protective activity, young plants are sprayed with the formulation of the active compound in the stated application amount. After the spray coating has dried on, the plants are inoculated with an aqueous spore suspension of Phytophthora infestans. The plants are then placed in an incubation cabin at about 20° C. and 100% relative atmospheric humidity.

Evaluation is carried out 3 days after the inoculation. In this evaluation, 0% means a degree of action which corresponds to that of the control, while a degree of action of 100% means that no infestation is observed.

In this test, the substance according to the invention described in Example (1) shows a degree of action of 90% or more at an application amount of 100 g/ha.

EXAMPLE B

Plasmopara test (vine)/protective
Solvent: 47 parts by weight of acetone
Emulsifier: 3 parts by weight of alkylaryl polyglycol ether To prepare an appropriate formulation of the active compound, 1 part by weight of active compound is mixed with the stated amounts of solvent and emulsifier, and the concentrate is diluted with water to the desired concentration.

To test for protective activity, young plants are sprayed with the formulation of the active compound in the stated application amount. After the spray coating has dried on, the plants are inoculated with an aqueous spore suspension of Plasmopara viticola and then remain in an incubation cabin at about 20° C. and 100% relative atmospheric humidity for 1 day. The plants are then placed in a greenhouse at about 21° C. and about 90% relative atmospheric humidity for 5 days. The plants are then moistened and placed in an incubation cabin for 1 day.

Evaluation is carried out 6 days after the inoculation. In this evaluation, 0% means a degree of action which corresponds to that of the control, while a degree of action of 100% means that no infestation is observed.

In this test, the substance according to the invention described in Example (1) shows a degree of action of 90% or more at an application amount of 100 g/ha.

EXAMPLE C

Pyricularia test (rice)/protective
Solvent: 2.5 parts by weight of acetone
Emulsifier: 0.06 part by weight of alkylaryl polyglycol ether To prepare an appropriate formulation of the active compound, 1 part by weight of active compound is mixed with the stated amount of solvent, and the concentrate is diluted with water and the stated amount of emulsifier to the desired concentration.

To test for protective activity, young rice plants are sprayed with the formulation of the active compound in the stated application amount. After the spray coating has dried on, the plants are inoculated with an aqueous spore suspension of Pyricularia oryzae. The plants are then placed in a greenhouse at 100% relative atmospheric humidity and 25° C.

Evaluation is carried out 4 days after the inoculation. In this evaluation, 0% means a degree of action which corresponds to that of the control, while a degree of action of 100% means that no infestation is observed.

In this test, the substances according to the invention described in Examples (1) and (2) show a degree of action of 70% or more at an application amount of 750 g/ha.

EXAMPLE D

Leptosphaeria nodorum test (wheat)/curative
Solvent: 10 parts by weight of N-methyl-pyrrolidone
Emulsifier: 0.6 part by weight of alkylaryl polyglycol ether To prepare an appropriate formulation of the active compound, 1 part by weight of active compound is mixed with the stated amounts of solvent and emulsifier, and the concentrate is diluted with water to the desired concentration.

To test for curative activity, young plants are sprayed with a conidia suspension of Leptosphaeria nodorum. The plants remain in an incubation cabin at 20° C. and 100% relative atmospheric humidity for 48 hours and are then sprayed with the formulation of the active compound in the stated application amount.

The plants are placed in a greenhouse at a temperature of about 15° C. and a relative atmospheric humidity of about 80%.

Evaluation is carried out 10 days after the inoculation. In this evaluation, 0% means a degree of action which corresponds to that of the control, while a degree of action of 100% means that no infestation is observed.

In this test, the substance according to the invention described in Example (1) shows a degree of action of 95% or more at an application amount of 250 g/ha.

EXAMPLE E

Leptosphaeria nodorum test (wheat)/protective
Solvent: 25 parts by weight of N,N-dimethylacetamide
Emulsifier: 0.6 part by weight of alkylaryl polyglycol ether To test for appropriate formulation of the active compound, 1 part by weight of active compound is mixed with the stated amounts of solvent and emulsifier, and the concentrate is diluted with water to the desired concentration.

To test for protective activity, young plants are sprayed with the formulation of the active compound in the stated application amount. After the spray coating has dried on, the plants are sprayed with a spore suspension of Leptosphaeria nodorum. The plants remain in an incubation cabin at 20° C. and 100% relative atmospheric humidity for 48 hours.

The plants are placed in a greenhouse at a temperature of about 15° C. and a relative atmospheric humidity of 80%.

Evaluation is carried out 10 days after the inoculation. In this evaluation, 0% means a degree of action which corresponds to that of the control, while a degree of action of 100% means that no infestation is observed.

In this test, the substance according to the invention described in Example (1) shows a degree of action of 90% or more at an application amount of 250 g/ha.

EXAMPLE F

Puccinia test (wheat)/protective
Solvent: 25 parts by weight of N,N-dimethylacetamide
Emulsifier: 0.6 part by weight of alkylaryl polyglycol ether To prepare an appropriate formulation of the active compound, 1 part by weight of active compound is mixed with the stated amounts of solvent and emulsifier, and the concentrate is diluted with water to the desired concentration.

To test for protective activity, young plants are sprayed with the formulation of the active compound in the stated application amount. After the spray coating has dried on, the plants are sprayed with the conidia suspension of Puccinia. The plants remain in an incubation cabin at 20° C. and 100% relative atmospheric humidity for 48 hours.

The plants are then placed in a greenhouse at a temperature of about 20° C. and a relative atmospheric humidity of 80% in order to promote the development of rust pustules.

Evaluation is carried out 10 days after the inoculation. In this evaluation, 0% means a degree of action which corresponds to that of the control, while a degree of action of 100% means that no infestation is observed.

In this test, the substance according to the invention described in Example (1) shows a degree of action of 90% or more at an application amount of 250 g/ha.

EXAMPLE G

Puccinia test (wheat)/curative
Solvent: 10 parts by weight of N,N-dimethylacetamide
Emulsifier: 0.6 part by weight of alkylaryl polyglycol ether To prepare an appropriate formulation of the active compound, 1 part by weight of active compound is mixed with the stated amounts of solvent and emulsifier, and the concentrate is diluted with water to the desired concentration.

To test for curative activity, young plants are sprayed with a conidia suspension of Puccinia recondite The plants remain in an incubation cabin at 20° C. and 100% relative atmospheric humidity for 48 hours. The plants are then sprayed with the active compound formulation in the stated application amount.

The plants are placed in a greenhouse at a temperature of about 20° C. and a relative atmospheric humidity of about 80% in order to promote the development of rust pustules.

Evaluation is carried out 10 days after the inoculation. In this evaluation, 0% means a degree of action which corresponds to that of the control, while a degree of action of 100% means that no infestation is observed.

In this test, the substance according to the invention described in Example (1) shows a degree of action of 100% or more at an application amount of 250 g/ha.

Patent claims:
1. A compound of the formula (I)

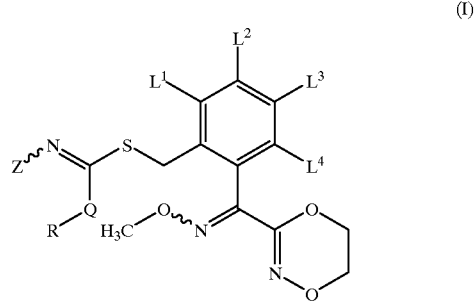

in which
Q represents a single bond, oxygen or sulphur,
R represents alkyl or optionally substituted cycloalkyl having 3 to 5 carbon atoms, Z represents in each case optionally substituted cycloalkyl, aryl, arylalkyl, heterocyclyl or heterocyclylalkyl and L$^1$, L$^2$, L$^3$ and L$^4$ are identical or different and independently of one another in each case represent hydrogen, halogen, cyano, nitro or in each case optionally halogen-substituted alkyl, alkoxy, alkylthio, alkylsulphinyl or alkylsulphonyl.

2. The compound of the formula (I) according to claim 1, in which

Q represents a single bond, oxygen or sulphur,

R represents alkyl having 1 to 4 carbon atoms or cycloalkyl having 3 to 6 carbon atoms which is optionally monosubstituted to tetrasubstituted by halogen or alkyl, Z represents cycloalkyl or cycloalkylalkyl which has in each case 3 to 7 carbon atoms in the cycloalkyl part and 1 to 4 carbon atoms in the alkyl part and is in each case optionally monosubstituted to tetrasubstituted by halogen or alkyl;

or represents heterocyclyl or heterocyclylalkyl which has in each case 3 to 7 ring members and 1 to 4 carbon atoms in the alkyl part and is optionally substituted by halogen or alkyl having 1 to 4 carbon atoms;

or represents aryl or arylalkyl which has in each case 6 to 10 carbon atoms in the aryl part and 1 to 4 carbon atoms in the alkyl part and is in each case optionally monosubstituted to tetrasubstituted in an identical or different manner in the aryl part, possible substituents selected from the group consisting of halogen, cyano, nitro, amino, formyl, carbamoyl, thiocarbamoyl;

in each case straight-chain or branched alkyl, alkoxy, alkoxyalkyl, alkylthioalkyl, alkylaminoalkyl, dialkylaminoalkyl, alkylthio, alkylsulphinyl or alkylsulphonyl having in each case 1 to 8 carbon atoms;

in each case straight-chain or branched alkenyl or alkenyloxy having in each case 2 to 6 carbon atoms;

in each case straight-chain or branched halogenoalkyl, halogenoalkoxy, halogenoalkylthio, halogenoalkylsulphinyl or halogenoalkylsulfonyl having in each case 1 to 6 carbon atoms and 1 to 13 identical or different halogen atoms;

in each case straight-chain or branched halogenoalkenyl or halogenoalkenyloxy having in each case 2 to 6 carbon atoms and 1 to 11 identical or different halogen atoms;

in each case straight-chain or branched alkylamino or dialkylamino;

alkylcarbonyl, alkoxycarbonyl, alkylaminocarbonyl, dialkylaminocarbonyl, arylalkylaminocarbonyl, alkenylcarbonyl or alkinylcarbonyl, having 1 to 6 carbon atoms in the particular hydrocarbon chains;

cycloalkyl or cycloalkyloxy having in each case 3 to 6 carbon atoms;

in each case divalent alkylene having 3 or 4 carbon atoms, oxyalkylene having 2 or 3 carbon atoms or dioxyalkylene having 1 or 2 carbon atoms, in each case optionally monosubstituted to tetrasubstituted in an identical or different manner by fluorine, chlorine, oxo, methyl, trifluoromethyl or ethyl;

and a grouping

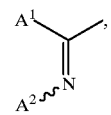

wherein

A$^1$ represents hydrogen or alkyl having 1 to 4 carbon atoms or cycloalkyl having 3 to 6 carbon atoms and A$^2$ represents hydroxyl, amino, methylamino, methyl, phenyl, benzyl, alkoxy, alkylamino or dialkylamino having 1 to 4 carbon atoms in the particular alkyl chains and L$^1$, L$^2$, L$^3$ and L$^4$ are identical or different and independently of one another in each case represent hydrogen, halogen, cyano, nitro or alkyl, alkoxy, alkylthio, alkylsulphinyl or alkylsulphonyl which has in each case 1 to 6 carbon atoms and is in each case optionally substituted by 1 to 5 halogen atoms, preferably hydrogen or methyl, and in particular hydrogen.

3. The compound of the formula (I) according to claim 1, in which

Q represents a single bond, oxygen or sulphur,

R represents methyl, ethyl, n- or i-propyl or, in particular, cyclopropyl, cyclobutyl or cyclopentyl, in each case optionally monosubstituted to tetrasubstituted by fluorine, chlorine, methyl or ethyl.

Z represents cyclopentyl or cyclohexyl, in each case optionally monosubstituted to tetrasubstituted by fluorine, chlorine, methyl or ethyl;

or represents thienyl, pyridyl, furyl, thienylmethyl, pyridylmethyl or furylmethyl, optionally substituted by methyl, ethyl, fluorine, chlorine or bromine;

or represents benzyl, 1-phenylethyl or 2-phenylethyl, in each case optionally monosubstituted to tetrasubstituted in an identical or different manner, and in particular represents optionally substituted phenyl, possible substituents selected from the group consisting of:

fluorine, chlorine, bromo, cyano, nitro, amino, formyl, carbamoyl, thiocarbamoyl, methyl, ethyl, n- or i-propyl, n-, i-, s- or t-butyl, methoxymethyl, methoxy, ethoxy, n- or i-propoxy, methylthio, ethylthio, n- or i-propylthio, methylsulphinyl, ethylsulphinyl, methylsulphonyl or ethylsulphonyl, methylaminomethyl, dimethylaminomethyl, vinyl, allyl, 2-methylallyl, propen-1-yl, crotonyl, propargyl, vinyloxy, allyloxy, 2-methylallyloxy, propen-1-yloxy, crotonyloxy, propargyloxy; trifluoromethyl, trifluoroethyl, difluoromethoxy, trifluoromethoxy, difluorochloromethoxy, trifluoroethoxy, pentafluoroethoxy, 2-chloro-1,1,2-trifluoroethoxy, difluoromethylthio, trifluoromethylthio, difluorochloromethylthio, trifluoromethylsulphinyl or trifluoromethylsulphonyl, methylamino, ethylamino, n- or i-propylamino, dimethylamino, diethyl-amino, acetyl, propionyl, methoxycarbonyl, ethoxycarbonyl, methylaminocarbonyl, ethylaminocarbonyl, dimethylaminocarbonyl, diethylaminocarbonyl, acryloyl, propioloyl, cyclopentyl, cyclohexyl, in each case divalent propanediyl, ethyleneoxy, methylenedioxy or ethylenedioxy, in each case optionally monosubstituted to tetrasubstituted in an identical or different manner by fluorine, chlorine, oxo, methyl or trifluoromethyl,
and a grouping

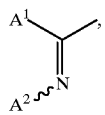

wherein
$A^1$ represents hydrogen or methyl and
$A^2$ represents hydroxyl, methoxy, ethoxy, amino, methylamino, methyl, phenyl or benzyl and
$L^1, L^2, L^3$ and $L^4$ are identical or different and independently of one another in each case represent hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoro-methylthio, trifluoromethylsulphinyl or trifluoromethylsulphonyl, preferably hydrogen or methyl, and in particular hydrogen.

4. A fungicidal composition characterized by a content of at least one compound of the formula (I) according to claim 1 and an extender and/or a surfactant.

5. A method of combating pests, characterized in that compounds of the formula (I) according to claim 1 are allowed to act on pests and/or their environment.

6. A process for the preparation of compositions comprising mixing compounds of the formula (I) according to claim 1 with extenders and/or surface-active agents.

7. A process for the preparation of compounds of the formula (I) as defined in claim 1 comprising reacting a thioamide of the general formula (II)

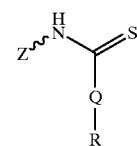

in which
Q, R and Z have the abovementioned meanings,
with a halogenomethyl compound of the general formula (III)

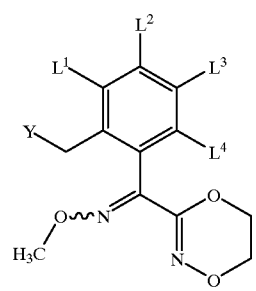

in which
$L^1, L^2, L^3$ and $L^4$ have the abovementioned meanings and
Y represents halogen,
optionally in the presence of a diluent and optionally in the presence of an acid acceptor.

* * * * *